(12) United States Patent
Buono

(10) Patent No.: US 6,802,829 B2
(45) Date of Patent: Oct. 12, 2004

(54) SPRAY DEVICE

(75) Inventor: Lawrence M. Buono, Philadelphia, PA (US)

(73) Assignee: Infinite Vision, LLC, Exton, PA (US)

(*) Notice: Subject to any disclaimer, the term of this patent is extended or adjusted under 35 U.S.C. 154(b) by 56 days.

(21) Appl. No.: 10/073,737

(22) Filed: Feb. 11, 2002

(65) Prior Publication Data
US 2003/0097117 A1 May 22, 2003

Related U.S. Application Data

(60) Provisional application No. 60/334,470, filed on Nov. 16, 2001, now abandoned.

(51) Int. Cl.[7] .................................... A61M 5/315
(52) U.S. Cl. ................ 604/218; 604/187; 604/264; 604/272; 606/167; 606/185
(58) Field of Search .................... 604/521, 27, 36, 604/38, 39, 93.01, 181, 187, 218, 257, 239–243, 264, 294, 170.01, 272–275; 600/3–5, 12; 222/386, 566, 575, 565; 433/89, 90; 606/167, 185

(56) References Cited

U.S. PATENT DOCUMENTS

| | | | | | |
|---|---|---|---|---|---|
| 2,899,959 | A | * | 8/1959 | Ginsburg | 604/174 |
| 3,739,779 | A | * | 6/1973 | Pfleger | 604/205 |
| 3,815,604 | A | * | 6/1974 | O'Malley et al. | 604/22 |
| 4,276,880 | A | * | 7/1981 | Malmin | 604/28 |
| 4,537,593 | A | * | 8/1985 | Alchas | 604/411 |
| 4,578,058 | A | * | 3/1986 | Grandon | 604/27 |
| 4,596,548 | A | * | 6/1986 | DeVries et al. | 604/6.16 |
| 4,735,612 | A | * | 4/1988 | Chevalier | 604/130 |
| 4,759,746 | A | * | 7/1988 | Straus | 604/512 |
| 4,767,416 | A | * | 8/1988 | Wolf et al. | 604/239 |
| 4,790,830 | A | * | 12/1988 | Hamacher | 604/274 |
| 4,808,170 | A | * | 2/1989 | Thornton et al. | 604/274 |
| 4,821,717 | A | * | 4/1989 | Wehrli | 606/44 |
| 4,909,784 | A | * | 3/1990 | Dubroff | 604/521 |
| 5,098,389 | A | * | 3/1992 | Cappucci | 604/158 |
| 5,100,390 | A | * | 3/1992 | Lubeck et al. | 604/158 |
| 5,127,831 | A | * | 7/1992 | Bab | 433/80 |
| 5,167,618 | A | | 12/1992 | Kershner | |
| 5,254,106 | A | * | 10/1993 | Feaster | 604/272 |
| 5,284,476 | A | * | 2/1994 | Koch | 604/274 |
| 5,478,328 | A | * | 12/1995 | Silverman et al. | 604/272 |
| 5,679,666 | A | * | 10/1997 | Clark | 514/179 |
| 5,788,667 | A | * | 8/1998 | Stoller | 604/22 |
| 5,792,099 | A | * | 8/1998 | DeCamp et al. | 604/506 |
| 6,004,302 | A | * | 12/1999 | Brierley | 604/264 |
| 6,135,984 | A | * | 10/2000 | Dishler | 604/264 |
| 6,299,603 | B1 | | 10/2001 | Hecker et al. | |
| 6,402,734 | B1 | * | 6/2002 | Weiss | 604/521 |
| 6,413,245 | B1 | * | 7/2002 | Yaacobi et al. | 604/264 |
| 6,422,865 | B1 | * | 7/2002 | Fischer | 433/81 |
| 6,494,868 | B2 | * | 12/2002 | Amar | 604/273 |
| 6,533,769 | B2 | * | 3/2003 | Holmen | 604/521 |
| 2003/0009132 | A1 | | 1/2003 | Schwartz et al. | |

FOREIGN PATENT DOCUMENTS

WO    WO 97/36622 A1    10/1997

* cited by examiner

Primary Examiner—Brian Casler
Assistant Examiner—Cris L. Rodriguez
(74) Attorney, Agent, or Firm—Caesar, Rivise, Bernstein, Cohen & Pokotilow, LTD.

(57) ABSTRACT

A spray or delivery device is arranged to dispense a dye into the anterior chamber of a human eye or other mammalian eye for the purpose of staining a specific ocular structure or tissue. An ocular structure of particular interest is the anterior lens capsule. The spray device includes a cannula having a distal end arranged for insertion into the anterior chamber of the eye. The cannula preferably has a dispensing orifice located at a side of the cannula offset from the distal end. The orifice preferably dispenses the fluid dye or stain in spray form. In one exemplary embodiment, the cannula has a fin extending radially outward from the cannula. In another exemplary embodiment, the cannula has a flared sleeve surrounding and extending from the orifice. In a method for conducting intra-ocular surgery, said delivery device would dispense a dye in a particular fashion so as to control its application to the intended target tissue, thereby limiting delivery of the dye to undesired surrounding tissue structures.

20 Claims, 4 Drawing Sheets

SPRAY DEVICE

This application claims benefit of U.S. Provisional Application 60/334,470, filed on Nov. 16, 2001, now abandoned.

FIELD OF THE INVENTION

The present invention relates to a device arranged for spraying or dispersing a fluid (e.g., a stain or dye). In particular, this invention relates to a delivery device arranged for spraying or dispensing the fluid to an intra-ocular surface in the anterior chamber of a human eye or another mammalian eye as part of a diagnostic or therapeutic endeavor (e.g., cataract surgery).

BACKGROUND OF THE INVENTION

During intra-ocular surgery it is often desirable to distinguish between different intra-ocular structures. One means of accomplishing this desired effect is to use an adjuvant dye or stain to differentiate between different structures. There are several different types of dyes used to stain intra-ocular structure, including but not limited to fluorescein, indocyanine green, methylene blue, and trypan blue. A list of some other possible dyes includes indigotindisulfonate, rose bengal, patent blue V, sulphan blue, tolonium chloride, lissamine green, brilliant blue, carbanthrene blue, erythrosine, and alphazurine.

One type of such an intra-ocular surgery is cataract surgery. In modern cataract surgery, it is desirable to easily distinguish the anterior lens capsule from surrounding structures and perform a continuous curvilinear capsulorrhexis so that the natural lens can be removed by phacoemulsification or other methods and replaced with an artificial lens.

A method of cataract surgery is as follows. A small paracentesis incision is made peripherally into the clear cornea. The aqueous humor of the anterior chamber is subsequently drained and replaced with air. A dye is then applied to the anterior lens surface (e.g., anterior lens capsule) using a delivery device (e.g., a syringe). The dye is allowed to contact the lens surface for an amount of time sufficient to stain that surface. Optionally, the dye solution is drained or irrigated (using balanced salt solution) from the anterior chamber. Next, the anterior chamber is filled with an optically clear viscoelastic polymer (e.g., hyaluronate, chondroitin sulfate). A rent is made in the anterior lens capsule using a cystotome and a continuous curvilinear capsulorrhexis is the made under direct visualization of the stained anterior lens capsule. Removal of the natural lens material may be accomplished by a variety of methods including phacoemulsification.

In the above-outlined step of removing the aqueous humor from the anterior chamber and replacing it with air, the lens assumes a convex configuration. This occurs because the fluid from the anterior chamber is replaced with air and the pressure in this compartment of the eye is lower than the pressure in the vitreous compartment of the eye and the lens is pushed forward. This physical phenomenon of the lens assuming a convex configuration can cause difficulty with the application of a dye or stain to the anterior lens capsule surface.

When the fluid dye or stain is applied to the anterior lens surface of an air-filled anterior chamber, it tends to roll off to one side and collect in the gutter space created by the iris lens interface and the angle of the anterior chamber. Because of this, the dye or stain must be massaged into the capsule to achieve adequate staining. This maneuver of massaging the dye into the lens capsule causes the risk of inadvertently tearing the capsule and thereby complicating the remainder of the surgical procedure. Also, a larger volume than is necessary to adequately stain the lens capsule must be utilized.

Furthermore, the current method of delivering a fluid dye or stain to the anterior chamber to stain the anterior lens capsule is accomplished in an uncontrolled fashion. The dye or stain is applied to the surface of the anterior lens capsule for an amount of time sufficient to stain that surface. Because of the current design of the tip of the cannula, the dye or stain encounters intra-ocular structures that are not intended and may have a deleterious effect, including a toxic effect as well as diminishing the effect of selective staining.

BRIEF SUMMARY OF THE INVENTION

The preferred delivery devices are arranged to dispense a dye or stain in a controlled fashion to a target tissue or structure (e.g., anterior lens capsule) located in the anterior chamber of an eye for differentiating the target tissue or structure during a surgical procedure or any diagnostic or therapeutic endeavor. The device is designed to control the area to which the dye or stain can be delivered, thereby eliminating detrimental effects resulting from dispensing the dye or stain in an undesired area. The delivery device is constructed to have the dye or stain exit from an orifice located on an inferior surface of the cannula as opposed to a currently used dispensing orifice located at the distal tip of the cannula. This new location allows an operating surgeon to more precisely control the area to which the dye or stain is applied, thereby sparing the neighboring intra-ocular structures from unwanted staining. A preferred dye for staining the target tissue or structure is indigo carmine, as discovered by the inventor of the present invention.

In an exemplary embodiment, a dispensing device arranged to deliver a fluid into an eye includes a reservoir, a cannula and a pressurizer. The reservoir is arranged to house the fluid to be delivered. The a cannula has a distal tip for insertion into the eye, is in fluid communication with the reservoir and includes an orifice located inward of the cannula's distal tip. The pressurizer (e.g., plunger or mechanism that applies pressure into the reservoir) is arranged to move the fluid from the reservoir through the orifice to an intra-ocular structure within the eye.

The cannula has a distal portion extending from a location inward of the orifice to the distal tip. As such, the device may also include a fin extending longitudinally around the distal portion. Further, the orifice may include a sleeve surrounding and extending from the orifice in a direction desired for the fluid delivery. Preferably, this sleeve is flared outward from the orifice.

Moreover, the orifice of the invention is preferably designed to disperse the dye or stain in a spray form rather than stream form, so as to allow the dye or stain to better adhere to the tissue or structure. In other words, the orifice is preferably arranged with an opening having a size and shape sufficient to discharge liquid in spray form. This feature obviates the need to massage the dye into the lens capsule and prevents the possibility of the complication of inadvertently tearing the lens capsule. Also, this spray feature further prevents the dye or stain from leaking onto adjacent tissue; thereby staining tissue or structures not intended to be stained. This spray feature also allows for delivery of a smaller amount of the dye or stain to the intra-ocular compartment, thereby reducing any potential toxic effect of the dye or stain.

In another exemplary embodiment, a method for delivering a fluid to an intra-ocular structure is disclosed. The method uses a spray device having the fluid in a reservoir, a cannula in fluid communication with the reservoir and having a distal tip and an orifice located inward of the distal tip, and a pressurizer arranged to move the fluid from the reservoir through the orifice. The method includes inserting the cannula through an opening of an eye, aligning the orifice over the intra-ocular structure, and spraying the intra-ocular structure with the fluid by moving the fluid from the reservoir through the orifice.

In yet another exemplary embodiment, a spray device arranged to deliver a fluid into a cavity includes a reservoir, a cannula and a pressurizer. The reservoir is arranged to house the fluid to be delivered. The cannula has a distal tip for access into the cavity, is in fluid communication with the reservoir, and includes an orifice located inward of the distal tip. The pressurizer is arranged to move the fluid from the reservoir through the orifice to a tissue within the cavity.

The described characteristics of the invention are easily discernable from the drawings. Moreover, further scope of applicability of the present invention will become apparent in the description given hereafter. However, it should be understood that the detailed description and specific examples, while indicating preferred embodiments of the invention, are given by way of illustration only, since the invention will become apparent to those skilled in the art from this detailed description.

BRIEF DESCRIPTION OF THE DRAWINGS

The invention will be described in conjunction with the following drawings, in which like-referenced numerals designate like elements, and wherein.

DETAILED DESCRIPTION OF THE PREFERRED EMBODIMENTS

This invention includes a spray device that delivers a fluid (e.g., a dye or stain) in a precise and controlled manner. A user controls the direction of delivering the dye or stain by directing the dispensing orifice. In one embodiment flared extensions on the sides of the cannula prevent the dye or stain from dispersing in a retrograde fashion. In another embodiment a flared sleeve around the dispensing orifice assists in controlled delivery of the dye or stain.

The spray device preferably delivers the fluid in spray form. While not being limited to a particular theory, the term spray form generally refers to fine droplets or vapor that scatter or fall from the orifice. In the exemplary embodiments described below the spray is generally a fluid moved by pressure out of the orifice. Example forms of spray include but are not limited to: aerosol, mist, atomized, rarified liquid, droplets, vapor, drizzle, froth, fog, splash, or sprinkle.

The term distal refers to the end or direction of the device that is applied toward an injection site for delivery. The term proximate refers to the end or direction of the device that is opposite the distal end. The structural elements described in the exemplary embodiments can by formed of any suitable material, e.g. plastic, metal, rubber.

Figure 1:
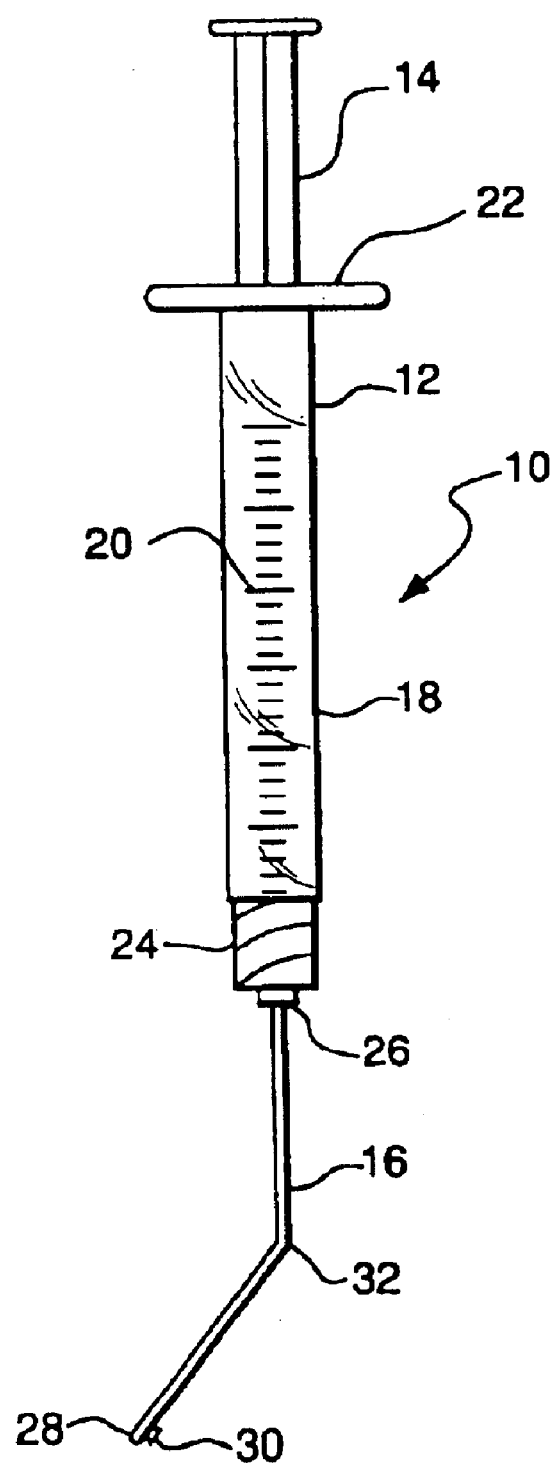
FIG. 1 is a top view of the invention including the reservoir and dispensing cannula with characteristic shape in accordance with an exemplary embodiment of the invention.

Referring to FIG. 1, a spray device is schematically illustrated at 10. The device 10 includes a reservoir 12, a plunger 14, and a cannula 16. The reservoir 12 is designed to store the dye or stain fluid that is intended to be delivered into the anterior chamber. Without being limited to a particular theory, the reservoir 12 is generally cylindrical in shape and has a surface 18 preferably with calibrated markings 20 imprinted thereon. The reservoir 12 is preferably constructed, at least in part, of a material that allows a user to see and measure fluid contained in the reservoir 12, such as a transparent or translucent plastic.

The plunger 14 extends within a first end 22 of the reservoir 12. The plunger 14 is mobile and is used as a pressurizer to assert pressure within the reservoir 12. While the plunger 14 is shown in FIG. 1 as having a particular form, a skilled artisan would readily understand that the plunger 14 could be of any mechanical, electrical or chemical form that allows the plunger 14 to assert pressure within the reservoir 12. As such, the plunger 14 can be separable or integral with the reservoir 12, and may have contact with other elements as desired to assert the pressure.

Referring in particular to FIG. 1, the reservoir 12 has a second end 24 with a cannula hub 26 that holds the cannula 16. Preferably the cannula hub 26 includes threads that allow for a coupling with opposing threads of the cannula 16. That is, the proximate end of the cannula 16 is arranged to be screwed into the threads of the cannula hub 26.

The cannula 16 includes a tip 28 and an orifice 30. The tip 28 is located at the distal end of the cannula 16, and is closed. That is, the tip 28 does not have an opening for dispensing fluid. While not being limited to a particular theory, a user (e.g., surgeon) cuts an incision in an eye and the cannula 16 is inserted into the eye through the incision. Accordingly, the cannula 16 is not used to poke through layered tissue. Because the cannula 16 is inserted through an existing incision, the tip 28 is preferably blunt. In fact, the tip 28 should be blunt and rounded to avoid accidental harm caused if the tip 28 was pressed or placed in contact with another object.

While not being limited to a particular theory, the cannula 16 is preferably a cylindrical hollow tube. As best seen in FIGS. 1, 3, 5 and 6, the body of the cannula 16 bends at an elbow 26 inward of the distal tip 28. The degree of the angle at the elbow 26 may be variable as desired with preferred angulation between about 15 degrees and about 60 degrees. The cannula 16 is bent at the elbow 26 to make it easier for a user (e.g., surgeon) to hold and control the spray device 10 during fluid delivery into an eye. In operation, the reservoir 12 and plunger 14 are arranged to extend away from the face of the patient, thereby keeping the user's fingers away from the patient's face. However, it is understood that the device 10 would work even if the cannula 16 were substantially straight along its entire length.

The dispensing orifice 30 is located inward of the tip 28 on the underside of the cannula 16. The orifice 30 is located on the underside of the cannula 16 to control the direction of delivery toward a specific intra-ocular structure, such as the anterior lens capsule in the anterior chamber. While not being limited to a particular distance, the orifice 30 is positioned a predetermined distance from the tip 28, preferably ranging from about 1 mm to about 3 mm inward of the tip 28. The orifice 30 is of sufficient size to dispense the fluid dye or stain in an spray fashion, as readily understood by a skilled artisan.

Figure 2:
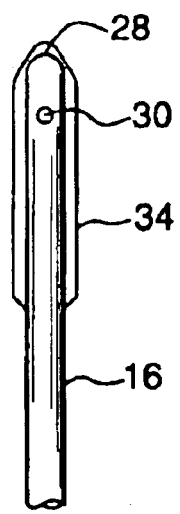
FIG. 2 is a partial side view of the cannula illustrated in FIG. 1.
Figure 3:
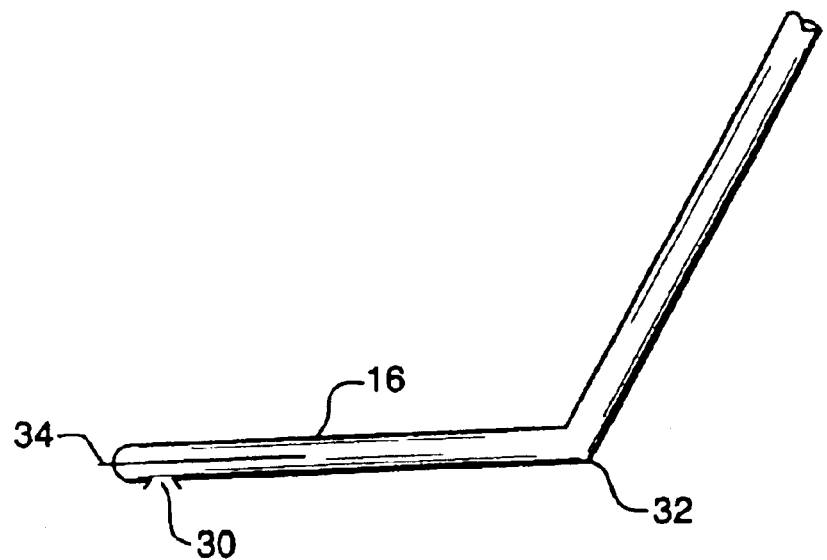
FIG. 3 is a partial top view of the cannula shown in FIG. 1.

FIGS. 2 and 3 illustrate a cannula 16 in accordance with an exemplary embodiment of the invention. As best seen in FIG. 2, the cannula 16 is attached to a fin 34 (e.g., flared extension) longitudinally attached to the sides and distal tip 28 of the cannula 16. The fin 34 is arranged to prevent the spray fluid dye or stain from projecting upward opposite the underside of the cannula 16. Accordingly, the fin 34 provides the benefit of preventing dispensed fluid from projecting away from the intended delivery site (e.g., anterior lens), thereby allowing for more controlled delivery of the fluid dye or stain. Preferably, the fin 34 extends away from the cannula 16 by a predefined distance at a plane substantially perpendicular to the underside of the cannula. The preferred distance is about 1 mm from the cannula tip 28, but may be constructed to be larger or smaller as desired. It is understood that the cannula 16 may be constructed without the fin 34 for situations where the cannula must be inserted through an incision too small to readily accept the fin 34.

Figure 4:
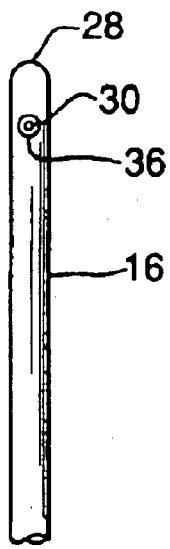
FIG. 4 is a partial side view of a cannula in accordance with another exemplary embodiment of the invention.
Figure 5:
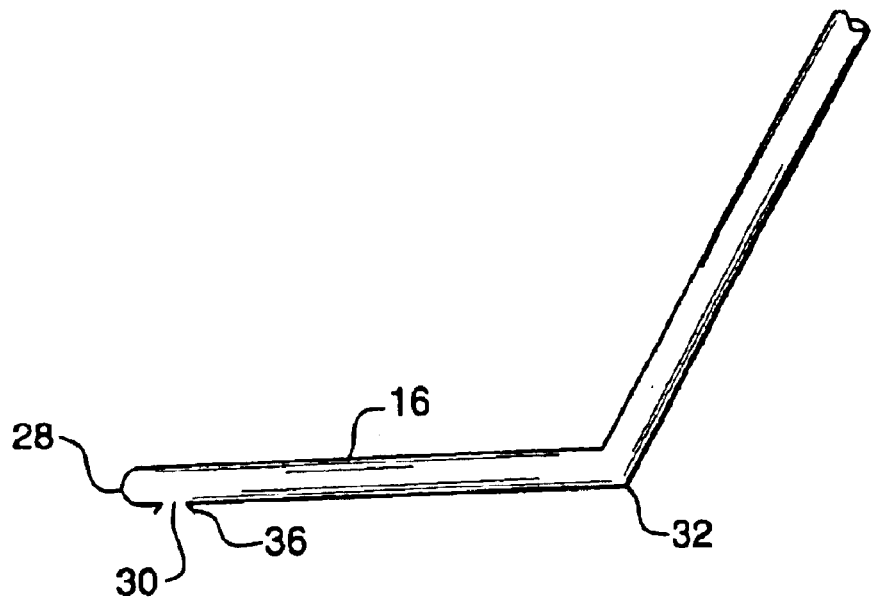
FIG. 5 is a partial top view of the cannula illustrated in FIG. 4.

FIGS. 4 and 5 illustrate a cannula 16 in accordance with another exemplary embodiment of the invention. Referring to FIGS. 4 and 5, a sleeve 36 surrounding the orifice 30 extends from the orifice 30 in a direction desired for the fluid delivery to further control the direction of the dye or stain dispersion. As shown by example in FIG. 5, the sleeve 36 extends a predefined distance from the base of the cannula 16 and projects outward at a flared angle. The preferred distance that the sleeve 36 projects from the cannula 16 is about 0.25 mm, although it is understood that the preferred distance depends on various factors, including the size of the cannula 16, the orifice 30, and incision.

The cannula 16 shown in FIGS. 4 and 5 is substantially similar to the cannula 16 shown in FIGS. 2 and 3. However, the cannula 16 shown in FIGS. 4 and 5 includes the sleeve 36 surrounding and extending from the orifice 30 in a direction desired for the fluid delivery, whereas the cannula 16 shown in FIGS. 2 and 3 includes the fin 34 extending longitudinally around its distal portion, as described in more detail above. It is understood that the spray device 10 could be constructed at least with either the sleeve 36 or the fin 34, or with both the sleeve 36 and the fin 34.

Figure 6:
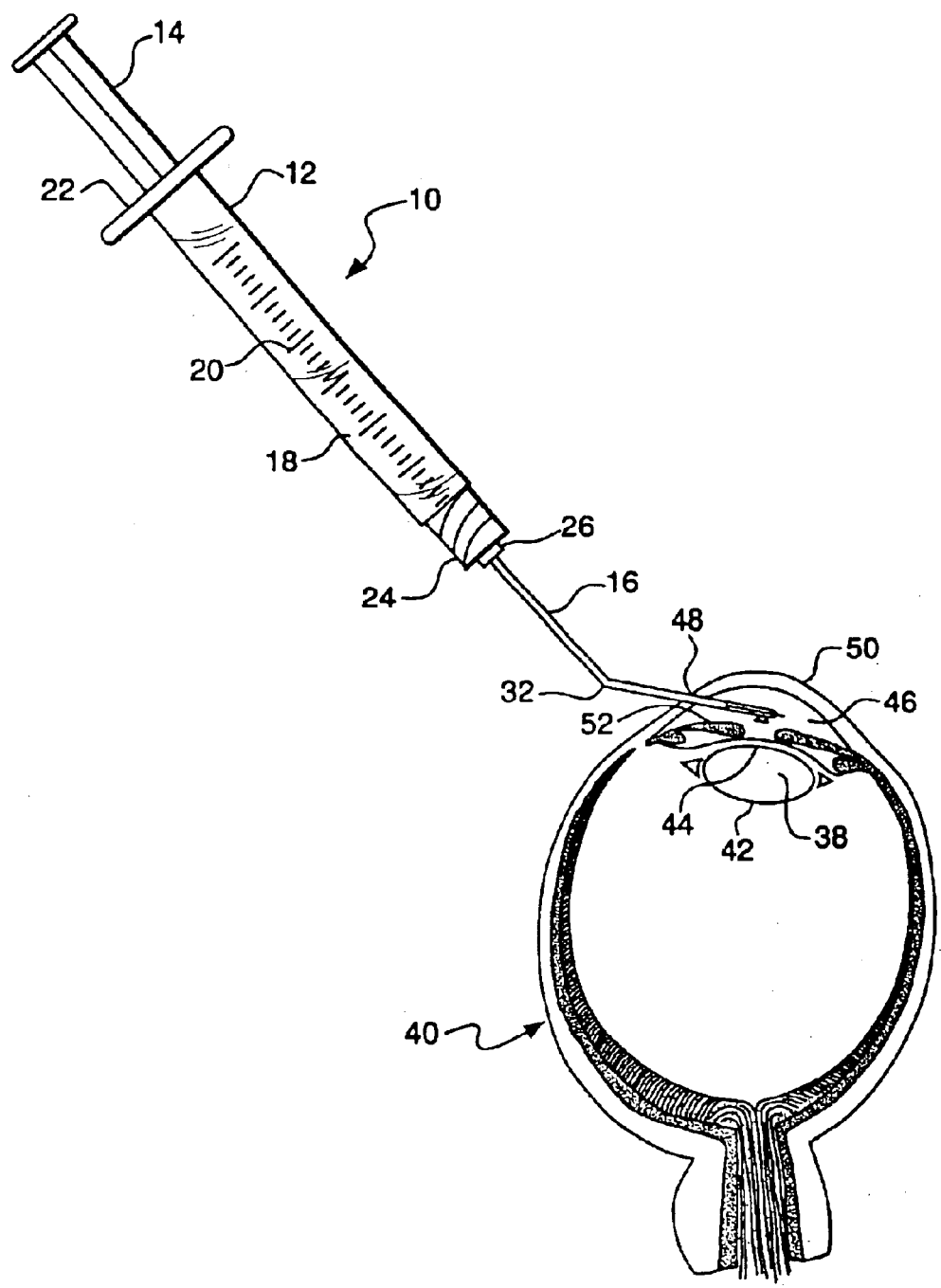
FIG. 6 is a top view of the cannula of FIG. 3 shown partially inserted in an anterior chamber of a human eye.

In FIG. 6, an exemplary delivery device 10 in accordance with the invention is illustrated in use during an operation, such as cataract surgery. During cataract surgery, a natural anterior lens 38 of an eye 40 is removed while leaving a lens capsule 42 in its natural anatomic location, and an artificial lens is inserted in place of the natural lens 38. To make the anterior lens 38 more easily visible to a surgeon, a fluid dye is delivered to a surface 44 of the lens to stain the surface. This can be accomplished by first draining aqueous fluid from an anterior chamber 46 of the eye 40 to provide an air-filled anterior chamber 46, and then by delivering the fluid dye into the air-filled chamber 46. The dye is allowed to contact the lens surface 44 for an amount of time sufficient to stain the surface 44, and then traditionally the excess dye may be drained out.

Referring to FIG. 6, the spray device 10 is shown with a portion of the cannula 16 inserted into the anterior chamber 46. In this procedure, the cannula 16 is inserted through a small paracentesis incision 48 at the cornea 50 of the eye 40. As shown in FIG. 6, the orifice 30 and flared sleeve 36 are preferably aligned between an iris 52 of the eye 40 for dispersing the fluid dye or stain onto the anterior lens surface 44. The fin 34 is also provided for preventing the fluid dye or stain from projecting upward opposite the dispensing orifice 30 side of the cannula 16 upon delivery of the fluid.

In operation, the user (e.g., surgeon) moves the plunger 14 into the reservoir 12, which moves fluid from the reservoir 12 through the cannula 16 and out of the orifice 30 onto the anterior lens surface 44 to stain the surface. Since the fluid dye is delivered directly to the lens surface 44, the fluid is more efficiently and more effectively delivered. Therefore there is no need to dispense excess amounts of dye as before to ensure that the lens 38 will be sufficiently stained. Accordingly there is no need for the additional step of draining excess fluid because there should be no more than an insubstantial amount of excess fluid in the anterior chamber 46.

The spray delivery device 10 of the invention thus makes it possible to control the dispersion of a fluid dye or stain during a surgical procedure or any diagnostic or therapeutic endeavor on a human or other mammalian eye 40. A skilled artisan would readily understand that the spray device could also be used during procedures in other areas, such as in medical procedures (e.g., dentistry, gynecology) where it is desirable to deliver a fluid to a particular region in a gaseous or air-filled environment.

It should be apparent from the aforementioned description and attached drawings that the concept of the present application may be readily applied to a variety of preferred embodiments, including those disclosed herein. For example, the cannula 16 shown in FIG. 2 could be constructed at least: with a sleeve 36 surrounding the orifice 30 as shown in FIG. 5, with a smaller sleeve 36 as shown in FIG. 3, or without a sleeve 36. Naturally, variant embodiments of the device of the invention can be used, providing they perform the same or equivalent functions as described above. Without further elaboration, the foregoing will so fully illustrate the invention that others may, by applying current or future knowledge, readily adapt the same for use under various conditions of service.

I claim:

1. A spray device arranged to deliver a fluid into an eye, comprising a reservoir arranged to house the fluid to be delivered, a cannula having a distal tip for insertion into the eye, said cannula in fluid communication with said reservoir and having an orifice located inward of said distal tip, said orifice including a sleeve surrounding and extending from said orifice in a direction desired for the fluid delivery and a pressurizer arranged to move the fluid from said reservoir throuph said orifice to an intra-occular structure within the eye, wherein the cannula is constructed so as to allow for the control of the direction of the fluid delivery.

2. The device of claim 1, wherein the cannula is arranged to deliver the fluid into the anterior chamber of the eye, and the orifice is located a predeteimined distance from the distal tip.

3. The device of claim 1, wherein said sleeve is flared outward from said orifice.

4. The device of claim 1, said cannula arranged for facilitating controlled dispersion of the fluid.

5. The device of claim 1, said pressurizer including a plunger inserted into said reservoir and arranged to deliver a specified aliquot of the fluid to the anterior chamber.

6. The device of claim 1, wherein the fluid is a dye or stain in liquid, aqueous, or gel form.

7. The device of claim 1, wherein said orifice is arranged to deliver the fluid towards the anterior lens capsule.

8. The device of claim 1, said reservoir including a cannula hub attached to said cannula.

9. The device of claim 8, further comprising an elbow at a bend in said cannula between said cannula hub and said distal tip.

10. The device of claim 1, wherein said orifice is structured to deliver the fluid in a spray form.

11. The device of claim 1, further comprising the fluid contained in said reservoir that is delivered into the eye.

12. The device of claim 11, wherein the fluid contained in said reservoir is indigo carmine.

13. The device of claim 1, wherein said distal tip is closed.

14. A spray device arranged to deliver a fluid into an eye, comprising a reservoir arranged to house the fluid to be delivered, a caunula having a distal tip for insertion into the eye, said cannula in fluid communication with said reservoir and having an orifice located inward of said distal tip, said caunula having a distal portion extendiug from a location inward of said orifice to said distal tip, said device further comprising a fin extending longitudinally around said distal portion and a pressurizer arranged to move the fluid from said reservoir through said orifice to an intra-ocular structure within the eye, wherein the cannula is constructed so as to allow for the control of the direction of the fluid delivery.

15. The device of claim 14, wherein said distal tip is closed.

16. A spary device arranged to deliver a fluid into a cavity, comprising a reservoir arranged to house the fluid to be delivered, a cannula having a distal tip for access into the cavity, said cannula in fluid communication with said reservoir and having an orifice located inward of said distal tip, said orifice including a sleeve surrounding and extending from said orifice in a direction desired for the fluid delivery, and a pressurizer arranged to move the fluid from said reservoir through said orifice to a tissue within the cavity.

17. The device of claim 16, wherein said sleeve is flared outward from said orifice.

18. The device of claim 16, wherein said distal tip is closed.

19. A spray device arranged to deliver a fluid into a cavity, comprising a reservoir arranged to house the fluid to be delivered, a cannula having a distal tip for access into the cavity, said cannula in fluid communication with said reservoir and having an orifice located inward of said distal tip, and a pressurizer arranged to move the fluid from said reservoir through said orifice to a tissue within the cavity, said cannula having a distal portion extending from a location inward of said orifice to said distal tip, said device further comprising a fin extending longitudinally around said distal portion.

20. The device of claim 19, wherein said distal tip is closed.

* * * * *